(12) United States Patent
Kawamoto et al.

(10) Patent No.: US 11,104,659 B2
(45) Date of Patent: *Aug. 31, 2021

(54) FUSED HETEROPOLYCYCLIC COMPOUND, AND METHOD FOR PRODUCING CONDUCTIVE POLYMER IN WHICH SAID COMPOUND IS USED

(71) Applicant: SHOWA DENKO K.K., Tokyo (JP)

(72) Inventors: Takeshi Kawamoto, Tokyo (JP); Yuka Niimi, Tokyo (JP)

(73) Assignee: SHOWA DENKO K.K., Tokyo (JP)

( * ) Notice: Subject to any disclaimer, the term of this patent is extended or adjusted under 35 U.S.C. 154(b) by 79 days.

This patent is subject to a terminal disclaimer.

(21) Appl. No.: 16/474,400

(22) PCT Filed: Sep. 29, 2017

(86) PCT No.: PCT/JP2017/035430
§ 371 (c)(1),
(2) Date: Jun. 27, 2019

(87) PCT Pub. No.: WO2018/123178
PCT Pub. Date: Jul. 5, 2018

(65) Prior Publication Data
US 2019/0337919 A1   Nov. 7, 2019

(30) Foreign Application Priority Data

Dec. 28, 2016 (JP) .............................. JP2016-254978

(51) Int. Cl.
*C07D 333/72* (2006.01)
*C08G 61/12* (2006.01)

(52) U.S. Cl.
CPC ......... *C07D 333/72* (2013.01); *C08G 61/126* (2013.01); *C08G 2261/228* (2013.01); *C08G 2261/3243* (2013.01); *C08G 2261/51* (2013.01)

(58) Field of Classification Search
CPC ................ C07D 333/72; C08G 61/126; C08G 2261/228; C08G 2261/3243; C08G 2261/51

See application file for complete search history.

(56) References Cited

U.S. PATENT DOCUMENTS 4,640,748 A    2/1987  Wudl et al.
5,648,453 A *  7/1997  Saida ................... C08G 61/123
                                                      525/410

FOREIGN PATENT DOCUMENTS

CN     85105974 A    2/1987
CN     1297569 A     5/2001
(Continued)

OTHER PUBLICATIONS

F. Wudl et al., "Poly(isothianaphthene)," Journal of Organic Chemistry, 1984, pp. 3382-3384, vol. 49, No. 18.

(Continued)

*Primary Examiner* — Shane Fang
(74) *Attorney, Agent, or Firm* — Sughrue Mion, PLLC (57) ABSTRACT

The present invention relates to a fused heteropolycyclic compound represented by formulae (1) and (2), a method for producing the same, and a method for producing a conductive polymer represented by formulae (3) and (4) in which at least one compound represented by formula (2) is used (the symbols in the formulae are as described in the description). The method of the present invention is a method for producing a sulfo-group-containing polyisothianaphthene capable of reducing the use amount of an oxidant or capable of being polymerized without the use of any oxidant.

5 Claims, 2 Drawing Sheets

WAVELENGTH (56) References Cited

FOREIGN PATENT DOCUMENTS

| | | |
|---|---|---|
| EP | 0 971 382 A1 | 1/2000 |
| JP | 61-12784 A | 1/1986 |
| JP | 63-118323 A | 5/1988 |
| JP | 05-310894 A | 11/1993 |
| JP | 07-48436 A | 2/1995 |
| JP | 2003-272874 A | 9/2003 |
| JP | 2010-195980 A | 9/2010 |

OTHER PUBLICATIONS

M. P. Cava et al., "Condensed Cyclobutane Compounds. VI. The Pyrolysis of 1,3-Dihydroisothianaphthene-2,2-dioxide: A New Synthesis of Benzocyclobutene," Journal of American Chemical Society, Aug. 20, 1959, pp. 4266-4268, vol. 81.
International Search Report of PCT/JP2017/035430 dated Dec. 26, 2017.

* cited by examiner

FUSED HETEROPOLYCYCLIC COMPOUND, AND METHOD FOR PRODUCING CONDUCTIVE POLYMER IN WHICH SAID COMPOUND IS USED

CROSS REFERENCE TO RELATED APPLICATIONS

This application is a National Stage of International Application No. PCT/JP2017/035430 filed Sep. 29, 2017, claiming priority based on Japanese Patent Application No. 2016-254978 filed Dec. 28, 2016.

TECHNICAL FIELD

The present invention relates to a fused heteropolycyclic compound and a method for producing a conductive polymer using the compound.

BACKGROUND ART

Polymers each having a π-conjugated double bond, typified by polyacetylene, polythiophene, polyaniline, polypyrrole, and the like, are each known to become a conductor (conductive polymer) through doping with an acceptor or a donor, and are under investigation for application to an antistatic agent, a solid electrolyte for a capacitor, a conductive coating material, an electrochromic device, a transparent electrode, a transparent conductive film, a chemical sensor, an actuator, and the like.

Of the above-mentioned conductive polymers, polyisothianaphthenes have the following features, which are not found in other conductive polymers: being stable in air; being easily doped with a general doping agent to show a high electric conductivity; and showing a reversible change in color ranging from blue to transparent through an electrochemical operation involving doping and dedoping.

As a method of producing a polymer having an isothianaphthene structure, there are known a chemical oxidative polymerization method involving using an oxidant (Patent Literature 1), and a method involving performing electrochemical oxidative polymerization (electrolytic polymerization) (Non Patent Literature 1).

However, many polymers each having an isothianaphthene structure are each an insoluble and infusible powder or mass. Accordingly, each of such polymers has poor molding performance, and hence, in order to be utilized as a conductive material, needs to be, for example, dispersed in an appropriate binder or processed by compression molding.

Meanwhile, a conductive polymer using isothianaphthene substituted with a sulfo group is soluble in water, and hence not only has satisfactory molding performance, but also contains a Bronsted acid group, such as a sulfo group, in a main chain of the polymer. Accordingly, the conductive polymer shows a stable conductive state over a long period of time without a contribution from any external dopant, and hence is drawing attention (Patent Literature 2).

CITATION LIST

Patent Literature

[PTL 1] JP 63-118323 A
[PTL 2] JP 07-48436 A (U.S. Pat. No. 5,648,453 A)

Non Patent Literature

[NPL 1] Journal of Organic Chemistry, 49, 3382-3384 (1984)

[NPL 2] Journal of the American Chemical Society, 81, 4266-4268 (1959)

SUMMARY OF INVENTION

Technical Problem

In the above-mentioned electrolytic polymerization for producing a polymer having isothianaphthene substituted with a sulfo group, a conductive polymer is produced in a film shape on an electrode, and hence the following problem arises: the shape and size of the conductive polymer are limited by the shape and size of the electrode, and hence expensive equipment is required, leading to a high cost.

In addition, when an oxidant is used in the preparation of the conductive polymer using isothianaphthene substituted with a sulfo group, the following problem arises: a sulfo group-substituted 1,3-dihydroisothianaphthene monomer is polymerized while undergoing four-electron oxidation, and hence a large amount of the oxidant is required.

Further, a π-electron-conjugated fused heteropolycyclic compound, such as isothianaphthene or naphtho[c]thiophene, has extremely high reactivity, and hence has a problem of being difficult to handle during production.

Therefore, an object of the present invention is to provide a novel fused heteropolycyclic compound capable of reducing the use amount of an oxidant as compared to that in a related-art method by undergoing two-electron oxidative polymerization, or capable of being polymerized without the use of any oxidant, and to provide a method for producing a sulfo group-containing polyisothianaphthene using the compound.

Solution to Problem

The inventors of the present invention have made extensive investigations in order to achieve the above-mentioned object, and as a result, have completed the present invention.

That is, the present invention provides the following novel fused heteropolycyclic compound, method for producing the same, and method for producing a conductive polymer using the compound.

[1] A fused heteropolycyclic compound, which is represented by the following formula (1):

where: $R^1$, $R^2$, $R^3$, $R^4$, and $R^5$ each independently represent a monovalent substituent selected from the group consisting of (1) a hydrogen atom, (2) a linear or branched alkyl group having 1 to 20 carbon atoms, a linear or branched alkoxy group having 1 to 20 carbon atoms, or a linear or branched alkyl ester group (alkylcarbonyloxy group or alkoxycarbonyl group) having 1 to 20 carbon atoms, (3) $SO_2M$, (4) a halogen atom, (5) a carboxy group, (6) a phosphonyl group, (7) a nitro group, (8) a cyano group, (9) a primary, secondary, or tertiary amino group, (10) a trihalomethyl group, (11) a phenyl group, and (12) a phenyl group substituted with at least one selected from an alkyl group, a hydroxy group, an alkoxy group, an alkyl ester group, a carbonyl group, a sulfo group, and a halogen atom; hydrocarbon chains in the substituents represented by $R^1$, $R^2$, $R^3$, $R^4$, and $R^5$ may be bonded to each other at any positions to form at least one divalent chain forming at least one cyclic structure of a three- to seven-membered cyclic saturated or unsaturated hydrocarbon together with carbon atoms to which the substituents are bonded; the alkyl group, the alkoxy group, or the alkyl ester group represented by each of $R^1$, $R^2$, $R^3$, $R^4$, and $R^5$, or the cyclic hydrocarbon chain formed thereby may contain at least one bond selected from a carbonyl, an ether, an ester, an amide, a sulfide, a sulfinyl, a sulfonyl, and an imino; M represents OH, or an alkali metal alkoxide selected from $O^-Na^+$, $O^-Li^+$, and $O^-K^+$, an ammonium alkoxide represented by $O^-NH_4^+$, a linear or branched alkoxy group having 1 to 20 carbon atoms, or a halogen atom selected from chlorine, fluorine, bromine, and iodine; and k represents the number of fused rings sandwiched between a heterocycle and a benzene ring having the substituents $R^1$ to $R^3$, and represents an integer of from 0 to 3.

[2] The fused heteropolycyclic compound according to the above-mentioned item 1, wherein k in the formula (1) represents 0.

[3] The fused heteropolycyclic compound according to the above-mentioned item 1 or 2, wherein M in the formula (1) is selected from OH, $O^-Na^+$, $O^-Li^+$, $O^-K^+$, and $O^-NH_4^+$.

[4] The fused heteropolycyclic compound according to any one of the above-mentioned items 1 to 3, wherein $R^1$, $R^2$, $R^3$, $R^4$, and $R^5$ in the formula (1) each independently represent a monovalent substituent selected from (1) a hydrogen atom, (2) a linear or branched alkyl group having 1 to 20 carbon atoms, a linear or branched alkoxy group having 1 to 20 carbon atoms, or a linear or branched alkyl ester group having 1 to 20 carbon atoms, (3) $SO_2M$, and (4) a halogen atom.

[5] A method for producing the fused heteropolycyclic compound of the above-mentioned item 1, the method including allowing an oxidant to act on a compound represented by the following formula (1A):

where: $R^1$, $R^2$, $R^3$, $R^4$, $R^5$, and M represent the same meanings as described for the formula (1); and k represents a number of fused rings sandwiched between a heterocycle and a benzene ring having the substituents $R^1$ to $R^3$, and represents an integer of from 0 to 3.

[6] A fused heteropolycyclic compound represented by the following formula (2):

where: $R^1$, $R^2$, $R^3$, $R^4$, $R^5$, and M represent the same meanings as described for the formula (1); and k represents a number of fused rings sandwiched between a heterocycle and a benzene ring having the substituents $R^1$ to $R^3$, and represents an integer of from 0 to 3.

[7] The fused heteropolycyclic compound according to the above-mentioned item 6, wherein k in the formula (2) represents 0.

[8] The fused heteropolycyclic compound according to the above-mentioned item 6 or 7, wherein $R^1$, $R^2$, $R^3$, $R^4$, and $R^5$ in the formula (2) each independently represent a monovalent substituent selected from (1) a hydrogen atom, (2) a linear or branched alkyl group having 1 to 20 carbon atoms, a linear or branched alkoxy group having 1 to 20 carbon atoms, or a linear or branched alkyl ester group having 1 to 20 carbon atoms, (3) a halogen atom selected from chlorine, fluorine, bromine, and iodine, and (4) $SO_2M$.

[9] A method for producing a fused heteropolycyclic compound represented by the formula (2), the method including allowing a Lewis acid to act on a fused heteropolycyclic compound represented by the following formula (1):

where symbols represent the same meanings as described for the formula (1) in the above-mentioned item 1.

[10] The method for producing a fused heteropolycyclic compound according to the above-mentioned item 9, wherein 0.1-fold equivalent to 30-fold equivalent of the Lewis acid is allowed to act with respect to the fused heteropolycyclic compound represented by the formula (1).

[11] A method for producing a conductive polymer containing as a monomer unit a structure represented by the following formula (3), the method including subjecting at least one kind of the fused heteropolycyclic compound represented by the formula (2) of the above-mentioned item 6 to two-electron oxidative polymerization:

(3)

where: $R^1$, $R^2$, $R^3$, $R^4$, $R^5$, M, and k represent the same meanings as described for the formula (1); and  represents a connection to an adjacent monomer unit.

[12] A method for producing a conductive polymer containing a chemical structure represented by the following formula (4), the method including subjecting at least one kind of the fused heteropolycyclic compound represented by the formula (2) of the above-mentioned item 6 to oxidative copolymerization with an aromatic compound capable of forming a thiophene, an isothianaphthene, a pyrrole, a furan, or the like:

(4)

where: $R^1$, $R^2$, $R^3$, $R^4$, $R^5$, M, and k represent the same meanings as described above; Ar represents a π-electron-conjugated repeating unit free of a sulfo group; and m and n represent mole fractions of respective monomer units in the copolymer, and hence m and n are not used for representing a block copolymer.

[13] The method for producing a conductive polymer according to the above-mentioned item 11 or 12, wherein the polymerization is performed by allowing an oxidant to act on the compound represented by the formula (2) of the above-mentioned item 6.

Advantageous Effects of Invention

The novel fused heteropolycyclic compounds each having a sulfo group represented by the formulae (1) and (2) of the present invention are more stable than isothianaphthene and naphtho[c]thiophene, and can each be easily handled in a unit operation in the production of the compound.

In the present invention, when an oxidant is allowed to act on the fused heteropolycyclic compound represented by the formula (2) having a sulfo group, the conductive polymer containing the chemical structure represented by the formula (3) or (4) can be efficiently produced with a small amount of the oxidant and under mild conditions.

As compared to a known conductive polymer, for example, a polythiophene derivative, the conductive polymer according to the present invention obtained by polymerizing the compound having the chemical structure represented by the formula (2) has a small energy gap as a semiconductor and shows high conductivity at a low doping level, and hence its conductive state is extremely stable. In addition, by virtue of the presence of the sulfo group as a substituent, a self-doped state can be easily expressed to provide a polymer having a stable electric conductivity.

Further, according to the present invention, not only a homopolymer, but also a copolymer can be easily produced by controlling copolymer composition constituting a π-conjugated main chain skeleton.

DESCRIPTION OF EMBODIMENTS

A novel fused heteropolycyclic compound and method for producing a conductive polymer using the compound according to embodiments of the present invention are described.

These embodiments are specifically described for a better understanding of the spirit of the invention, and do not limit the present invention unless otherwise specified.

The present invention relates to compounds represented by the following formulae (1) and (2), and methods of producing the same.

(1)

(2)

The present invention also relates to methods of producing conductive polymers represented by the following formulae (3) and (4).

(3)

(4)

Compounds Represented by Formulae (1) and (2)

An alkyl group, an alkoxy group, or an alkyl ester group represented by each of $R^1$, $R^2$, $R^3$, $R^4$, and $R^5$, or a cyclic hydrocarbon chain formed thereby may contain at least one bond selected from a carbonyl, an ether, an ester, an amide, a sulfide, a sulfinyl, a sulfonyl, and an imino.

In each of the formulae (1) and (2), the substituent M of a sulfonic acid represents any one of: OH; an alkali metal alkoxide, specifically $O^-Na^+$, $O^-Li^+$, or $O^-K^+$; a non-substituted, $C_1$ to $C_{30}$ alkyl-substituted, or $C_6$ to $C_{30}$ aryl-substituted alkoxide of a Group 15 element, such as $O^-NH_4^+$, $O^-NH(CH_3)_3^+$, $O^-N(CH_3)_4^+$, $O^-NH(C_2H_5)_3^+$, $O^-N(C_6H_5)_4^+$, $O^-PH_4^+$, $O^-P(CH_3)_4^+$, $O^-P(C_6H_5)_4^+$, $O^-AsH_4^+$, $O^-As(CH_3)_4^+$, or $O^-As(C_6H_5)_4^+$; a linear or branched saturated or unsaturated alkoxy group having 1 to 20 carbon atoms; a primary, secondary, or tertiary amino group; a trihalomethoxy group; a phenoxy group or a substituted phenoxy group; and a halogen atom selected from chlorine, fluorine, bromine, and iodine. The substituent serving as M may be a mixture of a plurality of different substituents.

In order to convert the metal in the alkoxide to a specific cation, ion exchange to any cation may be performed through a general ion-exchange resin or dialysis membrane.

k represents the number of fused rings sandwiched between a heterocycle and a benzene ring having the substituents $R^1$ to $R^3$, and represents an integer of from 0 to 3.

Useful examples of the substituents $R^1$, $R^2$, $R^3$, $R^4$, and $R^5$ include a hydrogen atom, a halogen atom, $SO_2M$, an alkyl group, an alkoxy group, an alkyl ester group, a nitro group, and a cyano group.

More specific examples of those substituents are given below. Examples of the halogen atom include fluorine, chlorine, bromine, and iodine. Examples of a hydrocarbon chain of the alkyl group or the alkyl ester group include methyl, ethyl, propyl, isopropyl, n-butyl, isobutyl, t-butyl, pentyl, hexyl, octyl, dodecyl, tetradecyl, cyclopentyl, and cyclohexyl. Examples of the alkoxy group include methoxy, ethoxy, (2-methoxy)ethoxy, propoxy, isopropoxy, hexyloxy, octyloxy, and dodecyloxy groups. Specific examples of the alkyl ester group include an alkylcarbonyloxy group and an alkoxycarbonyl group, such as a malonate group ($-OCOCH_2CO_2H$), a fumarate group ($-OCOCH=CHCO_2H$, the double bond is trans), and a maleate group ($-OCOCH=CHCO_2H$, the double bond is cis). The examples also include an alkylcarbonyloxy group and an alkoxycarbonyl group whose alkyl is methyl, ethyl, n-propyl, isopropyl, n-butyl, isobutyl, t-butyl, pentyl, hexyl, octyl, dodecyl, tetradecyl, cyclopentyl, or cyclohexyl.

Further, as substituents except the above-mentioned substituents, there are given, for example: amino groups, such as methylamino, ethylamino, diphenylamino, and anilino groups; and trifluoromethyl, chlorophenyl, and acetamide groups.

Hydrocarbon chains in the substituents represented by $R^1$, $R^2$, $R^3$, $R^4$, and $R^5$ may be bonded to each other at any positions to form at least one divalent chain forming at least one cyclic structure of a three- to seven-membered cyclic saturated or unsaturated hydrocarbon together with carbon atoms to which the substituents are bonded.

The alkyl group, the alkoxy group, or the alkyl ester group represented by each of $R^1$, $R^2$, $R^3$, $R^4$, and $R^5$, or the cyclic hydrocarbon chain formed thereby may contain at least one bond selected from a carbonyl, an ether, an ester, an amide, a sulfide, a sulfinyl, a sulfonyl, and an imino.

Examples in each of which the hydrocarbon chains of the substituents $R^1$, $R^2$, $R^3$, $R^4$, and $R^5$ in the formula (1) are bonded to each other at any positions to form a cyclic structure of a three- to seven-membered cyclic saturated or unsaturated hydrocarbon include structures represented by the following formulae (5) to (7).

(5)

(6)

(7)

k represents the number of fused rings sandwiched between a 1,3-dihydrothiophene-S-oxide ring and a benzene ring having the substituents $R^1$ to $R^3$ (formula (1)) or between a heterocycle and a benzene ring having the substituents $R^1$ to $R^3$ (formula (2)), and represents an integer of from 0 to 3. From the viewpoint of solubility in a solvent, k preferably represents 0.

A specific example of the basic skeleton moiety of the compound represented by the formula (1) excluding the substituents $R^1$ to $R^5$ and $SO_2M$ is 1,3-dihydroisothianaphthene-S-oxide (compound in which k represents 0).

Examples of the compound represented by the formula (1) include 1,3-dihydroisothianaphthene-S-oxide, 4-methyl-1,3-dihydroisothianaphthene-S-oxide, 5-methyl-1,3-dihydroisothianaphthene-S-oxide, 4,5-dimethyl-1,3-dihydroisothianaphthene-S-oxide, 5,6-dimethyl-1,3-dihydroisothianaphthene-S-oxide, 4,7-dimethyl-1,3-dihydroisothianaphthene-S-oxide, 5-fluoro-1,3-dihydroisothianaphthene-S-oxide, 5-chloro-1,3-dihydroisothianaphthene-S-oxide, 5-bromo-1,3-dihydroisothianaphthene-S-oxide, 5-hydroxy-1,3-dihydroisothianaphthene-S-oxide, and 5-carboxy-1,3-dihydroisothianaphthene-S-oxide.

A specific example of the basic skeleton moiety of the compound represented by the formula (2) excluding the substituents $R^1$ to $R^5$ and $SO_2M$ is isothianaphthene (compound in which k represents 0).

Examples of the compound represented by the formula (2) include isothianaphthene, 4-methylisothianaphthene, 5-methylisothianaphthene, 4,5-dimethylisothianaphthene, 5,6-dimethylisothianaphthene, 4,7-dimethylisothianaphthene, 5-fluoroisothianaphthene, 5-chloroisothianaphthene, 5-bromoisothianaphthene, 5-hydroxyisothianaphthene, and 5-carboxyisothianaphthene.

[Conductive Polymers Represented by Formulae (3) and (4)]

A conductive polymer containing as a monomer unit a structure represented by the formula (3) may be produced by subjecting at least one kind of the fused heteropolycyclic compound represented by the formula (2) to two-electron oxidative polymerization.

In addition, a conductive polymer containing a chemical structure represented by the formula (4) may be produced by subjecting at least one kind of the fused heteropolycyclic compound represented by the formula (2) to oxidative copolymerization with an aromatic compound capable of forming a thiophene, an isothianaphthene, a pyrrole, a furan, or the like. In each of the formulae (3) and (4), a plurality of kinds of the fused heteropolycyclic compounds represented by the formula (2) may be copolymerized.

In each of the formulae (3) and (4) representing the structure of a conductive polymer, $R^1$, $R^2$, $R^3$, $R^4$, $R^5$, M, and k represent the same meanings as $R^1$, $R^2$, $R^3$, $R^4$, $R^5$, M, and k in the formula (2), and specific examples thereof include the same ones as those shown as specific examples of $R^1$, $R^2$, $R^3$, $R^4$, $R^5$, and M in the formula (2).

In the formula (3), * represents a connection to an adjacent monomer unit, and in the formula (4), Ar represents a π-electron-conjugated monomer unit free of a sulfo group, and m and n represent the mole fractions of respective monomer units in the copolymer. m and n are not used for representing a block copolymer.

Examples of the aromatic compound capable of forming a thiophene, an isothianaphthene, a pyrrole, or a furan as used herein include isobenzofuran, isobenzoindoline, isobenzoselenophene, isobenzotellurophene, thiophene, pyrrole, furan, selenophene, tellurophene, aniline, and benzene.

The examples also include a 1,3-dihydro form, a 1,3-dihalogeno form, a 1,1,3,3-tetrahalogeno form, and a 2-oxide form of isothianaphthene, naphtho[2,3-c]thiophene, anthra[2,3-c]thiophene, naphthaceno[2,3-c]thiophene, pentaceno[2,3-c]thiophene, perylo[2,3-c]thiophene, and acenaphtho[2,3-c]thiophene, and derivatives thereof including various substituents, for example, a monovalent substituent selected from the group consisting of (2) a linear or branched alkyl group having 1 to 20 carbon atoms, a linear or branched alkoxy group having 1 to 20 carbon atoms, or a linear or branched alkyl ester group having 1 to 20 carbon atoms, (3) $SO_2M$, (4) a halogen atom, (5) a carboxy group, (6) a phosphonyl group, (7) a nitro group, (8) a cyano group, (9) a primary, secondary, or tertiary amino group, (10) a trihalomethyl group, (11) a phenyl group, and (12) a phenyl group substituted with at least one selected from an alkyl group, a hydroxy group, an alkoxy group, an alkyl ester group, a carbonyl group, a sulfo group, and a halogen. Of those, a 1,3-dihydro form of isobenzofuran, thiophene, pyrrole, furan, selenophene, or isothianaphthene, a 2-oxide form of isothianaphthene, and derivatives thereof are preferred. Preferred substituents include the same ones as those shown for the above-mentioned substituents $R^1$, $R^2$, $R^3$, $R^4$, and $R^5$.

In addition, 1,3-dihydrothieno[c]pyridine, 1,3-dihydrothieno[c]pyrazine, 1,3-dihydrothieno[c]pyridazine, and 1,3-dihydrothieno[c]quinoxaline each containing a nitrogen atom in a fused ring may also be used. In addition, the conductive polymer may contain two or more kinds of those aromatic compounds each having a π-electron-conjugated structure, fused heteropolycyclic compounds, and compounds each capable of forming a π-electron-conjugated structure after a reaction.

In each of the conductive polymers containing the chemical structures represented by the formulae (3) and (4) and each having a π-electron-conjugated structure in its main chain, when the substituent represented by M is OH, a self-doped state is exhibited in an aqueous solution even in the absence of any external dopant. In addition, solubility in various solvents and solvent affinity can be changed by changing the substituent represented by M.

The conductive copolymer containing the chemical structure represented by the formula (4) in the present invention is a copolymer containing at least one structural unit represented by the formula (3) as a monomer unit, and containing another π-electron-conjugated structural system as a monomer unit in the main chain structure of the polymer. The copolymer is produced by causing the compound represented by the formula (2) to coexist with at least one kind selected from other aromatic compounds, fused heteropolycyclic compounds, or compounds each capable of forming a π-electron-conjugated structure, or sequentially adding the compounds, to thereby polymerize the compounds.

In the conductive copolymer containing the chemical structure represented by the formula (4) in the present invention, m and n represent the mole fractions of the respective monomer units in the copolymer. Therefore, in the formula (4), m and n are not used for representing a block copolymer. With regard to the compositional mole fraction of the copolymer (m:n, provided that m+n=1), m representing the mole fraction of the monomer unit formed of the structural unit represented by the formula (3) falls within preferably the range of from 0.05 to 1.00, more preferably the range of from 0.10 to 0.90, still more preferably the range of from 0.20 to 0.80. When m represents 0.05 or more, no external dopant is required. In addition, when m represents from 0.50 to 1.00, a polymer having high hydrophilicity is obtained. As the ratio of m increases, the characteristic of being water soluble is more strongly exhibited.

[Method for Producing Compound Represented by Formula (1)]

A method for producing the fused heteropolycyclic compound represented by the formula (1) in the present invention is described.

A basic skeleton compound represented by the formula (1), specifically benzo[c]thiophene-1,3-dihydro-2-oxide and isothianaphthene (compound not substituted with —$SO_2M$) may be synthesized by methods described in "Journal of the American Chemical Society, 81, 4266-4268 (1959)" (Non Patent Literature 2) and "Journal of Organic Chemistry, 49(18), 3382-3384 (1984)" (Non Patent Literature 1). The heteropolycyclic compound free of —$SO_2M$ in the formula (1) may be synthesized by using acetic acid as an oxidant for 1,3-dihydroisothianaphthene described in Non Patent Literature 1.

A sulfo group may be introduced into the basic skeleton compound not substituted with —$SO_2M$ by allowing sulfuric acid, fuming sulfuric acid, sulfur trioxide, chlorosulfuric acid, fluorosulfuric acid, amidosulfuric acid, or the like for use in the sulfonation of a general aromatic compound to act on the basic skeleton compound. After that, a sulfonic acid methyl ester group may be introduced through the formation of sulfonyl chloride with chlorosulfuric acid, phosphorus pentachloride, or thionyl chloride, followed by a reaction with methanol.

Next, a method for producing the compound containing —$SO_2M$ of the present invention is described.

The fused heteropolycyclic compound represented by the formula (1) can be efficiently produced by allowing an oxidant to act on —$SO_2M$-containing 1,3-dihydroisothianaphthene represented by the formula (1A) under an elevated temperature, ordinary temperature, or low temperature, to thereby perform S-oxide formation.

Examples of the oxidant used for synthesizing the fused heteropolycyclic compound represented by the formula (1) include: oxygen; a peracid, such as hydrogen peroxide, persulfuric acid, ammonium persulfate, sodium persulfate, sodium periodate, peracetic acid, or meta-chloroperbenzoic acid; and a combination of a plurality of those oxidants.

The use amount of the oxidant varies depending on the kind of the oxidant and hence cannot be uniquely specified, but in general, the oxidant is used in the range of preferably from 0.1-fold equivalent to 6-fold equivalent, more preferably from 0.5-fold equivalent to 4-fold equivalent, still more preferably from 1-fold equivalent to 3-fold equivalent, with respect to the compound. When the use amount of the oxidant is from 0.1-fold equivalent to 6-fold equivalent, a sufficient yield is obtained, and the removal of the oxidant after the reaction is facilitated.

The concentration of the fused heteropolycyclic compound in the reaction system varies depending on the kind of the compound, a reaction scale, and the kinds of solvent and reagent, but in general, falls within the range of preferably from $10^{-3}$ mol/L to 10 mol/L, more preferably from $10^{-2}$ mol/L to 5 mol/L, still more preferably from $10^{-1}$ mol/L to 1 mol/L. When the concentration of the fused heteropolycyclic compound is from $10^{-3}$ mol/L to 10 mol/L, a sufficient reaction rate is obtained, and a side reaction hardly occurs.

A reaction temperature is determined according to each reaction method and cannot be particularly limited, but in general, falls within preferably the temperature range of from 0° C. to 250° C., more preferably the temperature range of from 20° C. to 200° C., still more preferably the temperature range of from 40° C. to 180° C. When the reaction temperature falls within the temperature range of from 0° C. to 250° C., a sufficient reaction rate and yield are obtained.

A reaction time varies depending on, for example, the reaction method, the reaction temperature, a reaction pressure, and the chemical structure of the fused heteropolycyclic compound, and hence cannot be uniquely defined, but in general, falls within the range of preferably from 0.1 hour to 72 hours, more preferably from 0.1 hour to 48 hours, still more preferably from 0.5 hour to 24 hours. When the reaction time is from 0.1 hour to 72 hours, a sufficient reaction rate and yield are obtained, and a side reaction hardly occurs. In addition, the reaction pressure in the reaction is preferably from $10^{-2}$ atm to 10 atm, more preferably from 0.1 atm to 5 atm, still more preferably normal pressure. When the reaction pressure is from $10^{-2}$ atm to 10 atm, a sufficient reaction rate is obtained.

The solvent to be used for the reaction may be any solvent that dissolves $10^{-3}$ mol/L or more of the fused heteropolycyclic compound. There may be used, for example: water; ethers, such as tetrahydrofuran, dioxane, and diethyl ether; polar solvents, such as dimethylformamide, acetonitrile, benzonitrile, N-methylpyrrolidone (NMP), dimethyl sulfoxide (DMSO), and N,N-dimethylformamide (DMF); esters, such as ethyl acetate and butyl acetate; and halogen-based solvents, such as chloroform and methylene chloride. Further, a mixed solvent thereof may be used.

[Method for Producing Compound Represented by Formula (2)]

The heteropolycyclic compound free of a sulfo group represented by the formula (2) may be synthesized by subjecting the compound of the above-mentioned formula (1) described in Non Patent Literature 2 to a dehydrogenation reaction by allowing aluminum oxide to act thereon.

In addition, the fused heteropolycyclic compound represented by the formula (2) can also be efficiently produced by subjecting the fused heteropolycyclic compound represented by the formula (1) to a dehydrogenation reaction by allowing a Lewis acid to act thereon under an elevated temperature, ordinary temperature, or low temperature.

Examples of the Lewis acid to be used for synthesizing the fused heteropolycyclic compound represented by the formula (2) include niobium pentoxide, aluminum oxide, and a combination of a plurality of those oxidants.

The use amount of the Lewis acid varies depending on the kind of the Lewis acid and hence cannot be uniquely specified, but in general, the Lewis acid is used in the range of preferably from 0.1-fold equivalent to 30-fold equivalent, more preferably from 1-fold equivalent to 25-fold equivalent, still more preferably from 5-fold equivalent to 20-fold equivalent, with respect to the fused heteropolycyclic compound represented by the formula (1). When the use amount of the Lewis acid is from 0.1-fold equivalent to 30-fold equivalent, a sufficient yield is obtained, and the removal of the Lewis acid after the reaction is facilitated.

The concentration of the fused heteropolycyclic compound in the reaction system varies depending on the kind of the compound, a reaction scale, and the kinds of solvent and reagent, but in general, falls within the range of preferably from $10^{-3}$ mol/L to 10 mol/L, more preferably from $10^{-2}$ mol/L to 5 mol/L, still more preferably from $10^{-1}$ mol/L to 1 mol/L. When the concentration of the fused heteropolycyclic compound is from $10^{-3}$ mol/L to 10 mol/L, a sufficient reaction rate is obtained, and a side reaction hardly occurs.

A reaction temperature is determined according to each reaction method and cannot be particularly limited, but in general, falls within preferably the temperature range of from 0° C. to 250° C., more preferably the temperature range of from 20° C. to 200° C., still more preferably the temperature range of from 40° C. to 180° C. When the reaction temperature falls within the temperature range of from 0° C. to 250° C., a sufficient reaction rate and yield are obtained.

A reaction time varies depending on, for example, the reaction method, the reaction temperature, a reaction pressure, and the chemical structure of the fused heteropolycyclic compound, and hence cannot be uniquely defined, but in general, falls within the range of preferably from 0.1 hour to 72 hours, more preferably from 0.1 hour to 48 hours, still more preferably from 0.5 hour to 24 hours. When the reaction time is from 0.1 hour to 72 hours, a sufficient reaction rate and yield are obtained, and a side reaction hardly occurs.

The solvent to be used for the reaction may be any solvent that dissolves $10^{-3}$ mol/L or more of the fused heteropolycyclic compound. There may be used, for example: water; ethers, such as tetrahydrofuran, dioxane, and diethyl ether; polar solvents, such as dimethylformamide, acetonitrile, benzonitrile, N-methylpyrrolidone (NMP), dimethyl sulfoxide (DMSO), and N,N-dimethylformamide (DMF); esters, such as ethyl acetate and butyl acetate; and halogen-based solvents, such as chloroform and methylene chloride. Further, a mixed solvent thereof may be used.

[Methods of Producing Conductive Polymers Represented by Formulae (3) and (4)]

A method for producing the conductive polymer containing the chemical structure represented by the formula (3) or the formula (4) in the present invention is described.

The polymer containing the chemical structure represented by the formula (3) or the formula (4) can be efficiently produced by polymerizing the compound represented by the formula (2) alone or in the coexistence of at least one kind selected from other aromatic compounds, fused heteropolycyclic compounds, or compounds each capable of forming a π-electron-conjugated structure, by allowing an oxidant to act thereon under an elevated temperature, ordinary temperature, or low temperature. The other aromatic compounds, fused heteropolycyclic compounds, or compounds each capable of forming a π-electron-conjugated structure are as described above.

In the oxidative polymerization reaction, examples of the oxidant that causes an oxidative dehydrogenation reaction include: oxidants each using a metal complex, such as iron(III) chloride, iron(II) chloride, iron ethylenediaminetetraacetate, copper(II) chloride, copper(I) chloride, copper ethylenediaminetetraacetate, or aluminum chloride; halogens, such as iodine and bromine; quinones, such as 2,3-dichloro-5,6-dicyano-1,4-benzoquinone, tetrachloro-1,2-benzoquinone, tetrachloro-1,4-benzoquinone, and tetracyano-1,4-benzoquinone; sulfonating agents, such as sulfuric acid, fuming sulfuric acid, sulfur trioxide, chlorosulfuric acid, fluorosulfuric acid, and amidosulfuric acid; oxygen; peracids, such as ammonium persulfate, sodium persulfate, and hydrogen peroxide; and a combination of a plurality of those oxidants. In addition, when the compound represented by the formula (2) has a function as an oxidant, the compound represented by the formula (2) undergoes polymerization even when alone.

The use amount of the oxidant varies depending on the kind of the oxidant, and hence cannot be uniquely specified, but in general, the oxidant is used in the range of preferably from 0.1-fold equivalent to 6-fold equivalent, more preferably from 0.5-fold equivalent to 4-fold equivalent, still more preferably from 1-fold equivalent to 4-fold equivalent with respect to the total amount of the compound represented by the formula (2) and the other aromatic compound having a π-electron-conjugated structure, fused heteropolycyclic compound, or compound capable of forming a π-electron-conjugated structure. When the use amount of the oxidant falls within the range of from 0.1-fold equivalent to 6-fold equivalent, a sufficient reaction rate and yield are obtained, and the removal of the oxidant after the reaction is facilitated.

The total concentration of monomers in the system in the polymerization reaction varies depending on the kinds of the monomers, a reaction scale, and the kinds of the solvent and the oxidant, but in general, falls within the range of preferably from $10^{-2}$ mol/L to 5 mol/L, more preferably from $10^{-2}$ mol/L to 3 mol/L, still more preferably from 0.05 mol/L to 1 mol/L. When the concentration of the monomers falls within the range of from $10^{-2}$ mol/L to 5 mol/L, a sufficient reaction rate and yield are obtained.

The reaction temperature of the polymerization reaction is determined according to each reaction method and cannot be particularly limited, but in general, the polymerization reaction is performed within preferably the temperature range of from 0° C. to 140° C., more preferably the temperature range of from 0° C. to 130° C., still more preferably the temperature range of from 20° C. to 130° C. When the reaction temperature falls within the temperature range of from 0° C. to 140° C., a sufficient reaction rate and yield are obtained, and a side reaction hardly occurs.

The reaction time of the polymerization reaction varies depending on, for example, the reaction method, the reaction temperature, a reaction pressure, and the chemical structure of the compound, and hence cannot be uniquely defined, but in general, falls within the range of preferably from 0.01 hour to 72 hours, more preferably from 0.1 hour to 48 hours, still more preferably from 0.5 hour to 48 hours. When the reaction time is from 0.01 hour to 72 hours, a side reaction hardly occurs, and a sufficient yield is obtained. In addition, the reaction pressure in the polymerization reaction is preferably from $10^{-2}$ atm to 10 atm, more preferably from 0.1 atm to 5 atm, still more preferably normal pressure. When the reaction pressure is from $10^{-2}$ atm to 10 atm, a sufficient reaction rate is obtained.

The solvent to be used for the polymerization reaction only needs to be one that dissolves the oxidant and does not inhibit the polymerization reaction. There are used, for example: water; ethers, such as tetrahydrofuran, dioxane, and diethyl ether; polar solvents, such as dimethylformamide, acetonitrile, benzonitrile, N-methylpyrrolidone (NMP), and dimethyl sulfoxide (DMSO); esters, such as ethyl acetate and butyl acetate; non-aromatic halogen-based solvents, such as chloroform and methylene chloride; and sulfuric acid, fuming sulfuric acid, formic acid, acetic acid, and propionic acid. A mixed solvent thereof may also be used. Of those, water, ethylene glycol, or dimethyl sulfoxide (DMSO) is preferred as the solvent.

The solvent may be volatilized during the progress of the reaction or after the reaction to provide a film-shaped polymer.

It is known that as the molecular weight of the conductive polymer obtained by polymerizing the fused heteropolycyclic compound represented by the formula (2) of the present invention increases, its absorption wavelength generally shifts to longer wavelengths. Accordingly, the degree of polymerization can be estimated in a simplified manner on the basis of an ultraviolet-visible-near infrared absorption spectrum or visual observation.

In addition, in the ultraviolet-visible-near infrared absorption spectrum, absorption at 1,000 nm or more indicates that the conductive polymer is doped. A higher absorbance at 1,000 nm or more indicates that a doping ratio, that is, a ratio at which a unit structure in the conductive polymer is doped is higher.

The conductive polymer obtained by polymerizing the fused heteropolycyclic compound represented by the formula (2) of the present invention may be mixed with another polymer or an additive to provide a composition. Specific examples of applications thereof include an antistatic agent, a solid electrolyte for a capacitor, a conductive coating material, an electrochromic device, a transparent electrode, a transparent conductive film, a chemical sensor, and an actuator.

EXAMPLES

The present invention is more specifically described below by way of Examples and Comparative Examples, but the present invention is not limited to Examples described below.

Evaluation methods are as described below.

<$^1$H-NMR Measurement>

Measurement was performed with an $^1$H-NMR measurement apparatus manufactured by JEOL Ltd. under the conditions of 400 MHz, CDCl$_3$ or DMSO-d$_6$, and 27° C.

<Yield>

After a reaction and post-treatment, the mass of the obtained amount of a fused heteropolycyclic compound was measured, and a yield was calculated by the following equation. The result is shown in Table 1.

Yield (%)=(mass of the actually obtained fused heteropolycyclic compound/mass of the obtained fused heteropolycyclic compound when reaction proceeds at reaction ratio of 100%)×100

<Ultraviolet-Visible-Near Infrared Absorption Spectrum>

An ultraviolet-visible-near infrared absorption spectrum was measured with an ultraviolet-visible-near infrared absorbance meter manufactured by Shimadzu Corporation using a quartz cell having an optical path length of 1 cm under the condition of 27° C.

<Observation of Reaction Liquid>

The colors of an obtained product and solution were visually observed.

Example 1: Production of Compound Represented by Formula (1) in which k=0, $R^1$=$R^2$=$R^3$=H, and M=O$^-$Na$^+$ A flask having a volume of 500 mL was loaded with 11.91 g (50 mmol) of known sodium 1,3-dihydroisothianaphthene-5-sulfonate and 200 mL of water (fused heteropolycyclic compound concentration: 0.25 mol/L). To the solution, 6.23 g (55 mmol: 1.1-fold equivalent with respect to the fused heteropolycyclic compound) of hydrogen peroxide water (30 mass % to 35.5 mass %) was added dropwise in small portions. After that, the contents were stirred under heating at 80° C. and normal pressure for 1.5 hours. After cooling to room temperature, the solvent was removed by evaporation under reduced pressure. At this time, in order to prevent hydrogen peroxide from being concentrated, a small amount of the solvent was allowed to remain instead of being brought to complete dryness. The resultant mixture was filtered, and washed with ethanol to remove hydrogen peroxide, to thereby afford 11.4 g of sodium 1,3-dihydroisothianaphthene-5-sulfonate-S-oxide as a pale yellow solid (45 mmol, yield: 90%).

$^1$H NMR (DMSO-d$_6$) δ 4.03 (dd, J$_{HH}$=16.0 Hz, 2H), 4.32 (d, J$_{HH}$=16.0 Hz, 2H), 7.34 (d, J$_{HH}$=8.0 Hz, 1H), 7.52 (d, J$_{HH}$=8.0 Hz, 1H), 7.63 (s, 1H).

MS (ESI) Calcd. for C$_8$H$_7$O$_4$S$_2$: 231.27 ([M-Na]$^-$), Obsd. 230.98 ([M-Na]$^-$).

Example 2: Production of Compound Represented by Formula (2) in which k=0, $R^1$=$R^2$=$R^3$=H, and M=O$^-$Na$^+$ A separable flask having a volume of 500 mL was loaded with 5.085 g (20 mmol) of sodium 1,3-dihydroisothianaphthene-5-sulfonate-S-oxide produced by the method described in Example 1, 79.74 g (300 mmol, 15-fold equivalent with respect to the fused heteropolycyclic compound) of activated aluminum oxide, and N,N'-dimethylformamide (35 mL) (fused heteropolycyclic compound concentration: 0.57 mol/L). The mixture was subjected to a reaction at 140° C. and normal pressure for 3 hours while being stirred using a stirring blade. After cooling to around room temperature, aluminum oxide was removed by filtration, followed by washing with water. The solvent was removed by evaporation under reduced pressure, and reprecipitation with water and acetone afforded 3.74 g of sodium isothianaphthene-5-sulfonate (15.8 mmol, yield: 79%) as a pale brown solid.

$^1$H NMR (DMSO-d$_6$) δ 7.23 (d, J$_{HH}$=8.0 Hz, 1H), 7.55 (d, J$_{HH}$=8.0 Hz, 1H), 7.84 (s, 1H), 7.93 (s, 1H), 8.04 (d, J$_{HH}$=6.0 Hz, 1H).

MS (ESI) Calcd. for C$_8$H$_5$O$_3$S$_2$: 213.26 ([M-Na]$^-$), Obsd. 212.97 ([M-Na]$^-$).

Example 3: Production of Compound Represented by Formula (1) in which k=0, $R^1$=$R^2$=$R^3$=H, and M=OCH$_3$ A flask having a volume of 500 mL was loaded with 11.91 g (50 mmol) of known sodium 1,3-dihydroisothianaphthene-5-sulfonate, 5 mL of DMF, and 250 mL of dichloromethane (fused heteropolycyclic compound concentration: 0.2 mol/L). Under a nitrogen atmosphere, while the contents were stirred, 7.2 mL (100 mmol, 2.0-fold equivalent with respect to the fused heteropolycyclic compound) of thionyl chloride was slowly added dropwise. The solution was heated to reflux under a nitrogen atmosphere for 3 hours. After that, the resultant was cooled to room temperature, and 4.2 g (50 mmol) of sodium hydrogen carbonate was added, followed by stirring at room temperature and normal pressure for 10 minutes. Celite filtration of the resultant solution afforded a dark brown solution. The solution was transferred to a flask having a volume of 500 mL, and while the solution was stirred at room temperature, 50 mL (50 mmol) of a 1 M solution of sodium methoxide in methanol was added dropwise in small portions. After stirring at room temperature for 30 minutes, the solvent was removed by evaporation under reduced pressure, and dichloromethane (200 mL) was added to the resultant mixture. The solution was washed by adding water, and then the organic layer was dried over anhydrous sodium sulfate and filtered. The resultant solution was transferred to a three-necked flask having a volume of 500 mL, and while the solution was stirred under cooling with ice, 8.50 mL (30 mass % to 35.5 mass %, 75 mmol) of a solution of hydrogen peroxide water in ethanol (50 mL) was added dropwise over 5 minutes or more. The solution was stirred at room temperature for 6 hours. After that, the solvent was removed by evaporation under reduced pressure, and dichloromethane was added. After washing by the addition of water, the organic layer was dried by adding anhydrous sodium sulfate and filtered. Reprecipitation with dichloromethane/hexane afforded 8.88 g of methyl 1,3-dihydroisothianaphthene-5-sulfonate-S-oxide (36.1 mmol, yield: 72%) as a pale yellow solid.

$^1$H NMR (CDCl$_3$) δ 3.78 (s, 3H), 4.28 (dd, $J_{HH}$=32.0 Hz, 4H), 7.59 (d, $J_{HH}$=4.0 Hz, 1H), 7.89 (d, $J_{HH}$=4.0 Hz, 1H), 7.95 (s, 1H).

MS (ESI) Calcd. for C$_9$H$_{11}$O$_4$S$_2$: 247.31 ([M+H]$^+$), Obsd. 247.21 ([M+H]$^+$).

Figure 1:
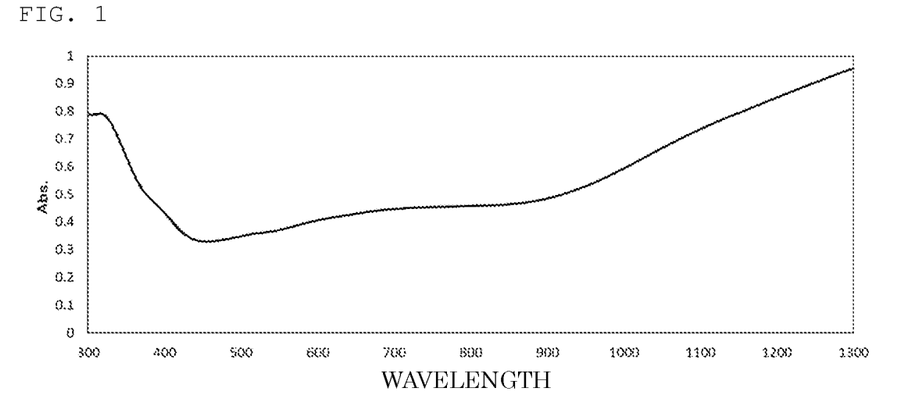
FIG. 1 is an ultraviolet-visible-near infrared absorption spectrum of a solution obtained in Example 4.

Example 4: Production of Polymer Represented by Formula (3) in which k=0, R$^1$=R$^2$=R$^3$=H, and M=O$^-$Na$^+$ A flask having a volume of 300 mL was loaded with 1.18 g (5 mmol) of sodium isothianaphthene-5-sulfonate produced by the method described in Example 2, 4.66 g (13 mmol) of disodium ethylenediaminetetraacetate, and 25 mL of water (m=1, monomer concentration: 0.2 mol/L). A solution of 2.03 g (13 mmol, 2.6-fold equivalent with respect to the monomers) of iron(III) chloride serving as an oxidant in water (25 mL) was added to initiate polymerization, and the mixture was stirred at room temperature under a normal-pressure atmosphere for 48 hours. The solution was placed in a beaker containing 125 mL of a cation-exchange resin and 125 mL of an anion-exchange resin that had been washed, and was stirred overnight to remove unnecessary ionic compounds, followed by filtration using a filter cloth. An ultraviolet-visible-near infrared absorption spectrum of the resultant polymer is shown in FIG. 1. The solution was dark blue, and in its ultraviolet-visible-near infrared absorption spectrum, peaks shifted to longer wavelengths (nm) to give a doped curve. It is considered that polymerization occurred.

Figure 2:
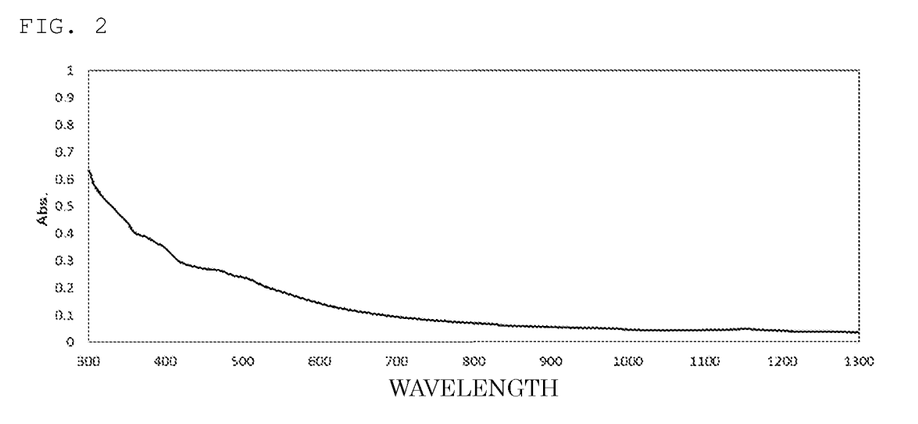
FIG. 2 is an ultraviolet-visible-near infrared absorption spectrum of a solution obtained in Comparative Example 1.

Comparative Example 1: Production of Polymer Represented by Formula (1A) in which k=0, R$^1$=R$^2$=R$^3$=H, and M=O$^-$Na$^+$ A flask having a volume of 300 mL was loaded with 1.19 g (5 mmol) of known sodium 1,3-dihydroisothianaphthene-5-sulfonate, 4.66 g (13 mmol) of disodium ethylenediaminetetraacetate, and 25 mL of water (m=1, monomer concentration: 0.2 mol/L). A solution of 2.03 g (13 mmol, 2.6-fold equivalent with respect to the monomers) of iron(III) chloride serving as an oxidant in water (25 mL) was added to initiate polymerization, and the mixture was stirred at room temperature under a normal-pressure atmosphere for 48 hours. The solution was placed in a beaker containing 125 mL of a cation-exchange resin and 125 mL of an anion-exchange resin that had been washed, and was stirred overnight to remove unnecessary ionic compounds, followed by filtration using a filter cloth. An ultraviolet-visible-near infrared absorption spectrum of the resultant polymer is shown in FIG. 2. The solution was pale brown. In the ultraviolet-visible-near infrared absorption spectrum, no absorption was found at wavelengths of 1,000 nm or longer, and hence doping was not confirmed. Thus, a conductive polymer was not obtained.

Figure 3:
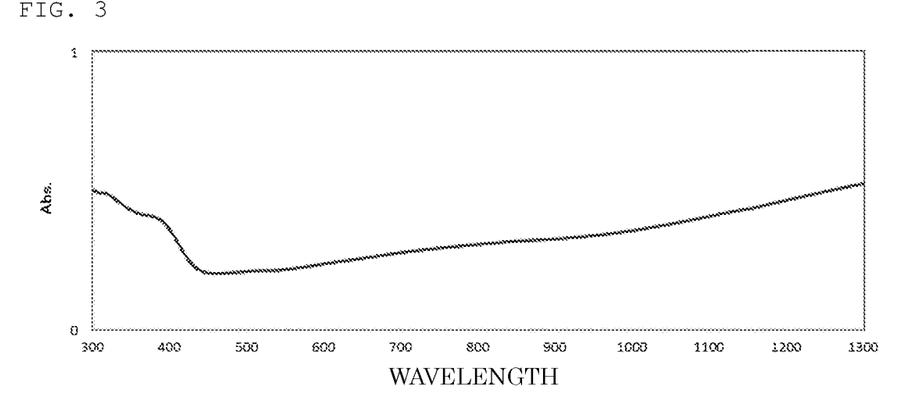
FIG. 3 is an ultraviolet-visible-near infrared absorption spectrum of a solution obtained in Example 5.

Example 5: Production of Polymer Represented by Formula (3) in which k=0, R$^1$=R$^2$=R$^3$=H, and M=O$^-$Na$^+$ A flask having a volume of 30 mL was loaded with 118.1 mg (0.5 mmol) of sodium isothianaphthene-5-sulfonate produced by the method described in Example 2, 18.6 mg (0.05 mmol) of disodium ethylenediaminetetraacetate, and 5 mL of water (m=1, monomer concentration: 0.1 mol/L). 8.1 mg (0.05 mmol, 0.1-fold equivalent with respect to the monomers) of iron(III) chloride serving as an oxidant was added to initiate polymerization, and the mixture was stirred at 80° C. under a normal-pressure atmosphere for 3.5 hours. The solution was placed in a beaker containing 1 mL of a cation-exchange resin and 1 mL of an anion-exchange resin that had been washed, and was stirred overnight to remove unnecessary ionic compounds, followed by filtration using a filter cloth. An ultraviolet-visible-near infrared absorption spectrum of the resultant polymer is shown in FIG. 3. The solution was dark blue, and in its ultraviolet-visible-near infrared absorption spectrum, peaks shifted to longer wavelengths (nm). It is considered that polymerization occurred.

Figure 4:
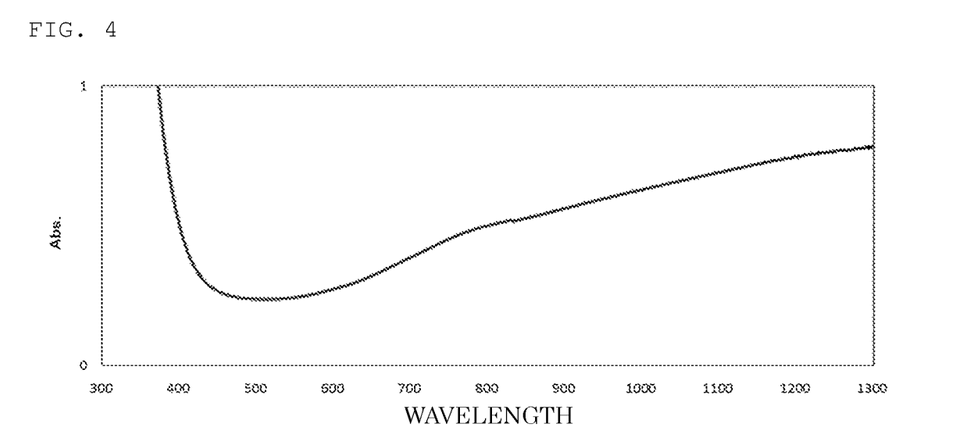
FIG. 4 is an ultraviolet-visible-near infrared absorption spectrum of a dispersion obtained in Example 6.

Example 6: Production of Copolymer Represented by Formula (4) in which k=0, R$^1$=R$^2$=R$^3$=H, M=O$^-$Na$^+$, and Ar=Ethylenedioxythiophene A flask having a volume of 300 mL was loaded with 1.65 g (7 mmol) of sodium isothianaphthene-5-sulfonate produced by the method described in Example 2, 427 mg (3 mmol) of known ethylenedioxythiophene, 9.31 g (25 mmol) of disodium ethylenediaminetetraacetate, and 50 mL of water, and the contents were vigorously stirred (copolymerization ratio: m=0.7, n=0.3, monomer concentration: 0.2 mol/L). A solution of 4.06 g (25 mmol, 3.6-fold equivalent with respect to the monomers) of iron(III) chloride serving as an oxidant in water (50 mL) was added to initiate polymerization, and the mixture was stirred at room temperature under a normal-pressure atmosphere for 48 hours. After 2 days, the disappearance of the two kinds of monomers (sodium isothianaphthene-5-sulfonate and ethylenedioxythiophene) was confirmed by $^1$H NMR. The dispersion was placed in a beaker containing 250 mL of a cation-exchange resin and 250 mL of an anion-exchange resin that had been washed, and was stirred overnight to remove unnecessary ionic compounds, followed by filtration using a filter cloth. An ultraviolet-visible-near infrared absorption spectrum of the resultant polymer is shown in FIG. 4. The dispersion was dark blue, and in the ultraviolet-visible-near infrared absorption spectrum, peaks shifted to longer wavelengths (nm), suggesting that polymerization occurred. In addition, the dispersion passed through a filter having a pore diameter of 5 μm without resistance.

Example 7: Production of Film with Conductive Polymer and Electric Conductivity Measurement The aqueous dispersion of the conductive polymer produced by the method described in Example 6 was applied to the surface of an alkali-free glass plate, and the resultant was dried by being placed on a hot plate heated to 100° C. for 10 minutes. As a result, a conductive polymer film having a thickness of 5 μm was obtained. The electric conductivity of the conductive polymer film at room temperature was measured with an electric conductivity meter manufactured by Mitsubishi Chemical Analytech Co., Ltd. using a PSP probe under the condition of 25° C., and was found to be G=5× 10$^{-3}$ S/cm. The value of the electric conductivity of the film under room temperature in air was stably maintained even after 3 months.

Example 8: Production of Film-Shaped Conductive Polymer 2.3 g (9.7 mmol) of the compound produced in Example 2 was added to 46.0 mL of ion-exchanged water (m=1, monomer concentration: 0.21 mol/L) and dissolved therein, and then the solution was passed through a column packed with a cation-exchange resin to remove sodium. Part of the resultant aqueous solution was dropped onto a glass plate, and heated to dryness under a normal-pressure atmosphere at 120° C. for 1 hour. The resultant was allowed to cool under a room-temperature atmosphere for a while. The produced solid was black, and a solution subjected to measurement obtained by adding the product to water was dark blue. In an ultraviolet-visible-near infrared absorption spectrum of the resultant solution, peaks shifted to longer wavelengths (nm), suggesting that polymerization occurred. In addition, the production of polyisothianaphthene was confirmed.

Figure 5:
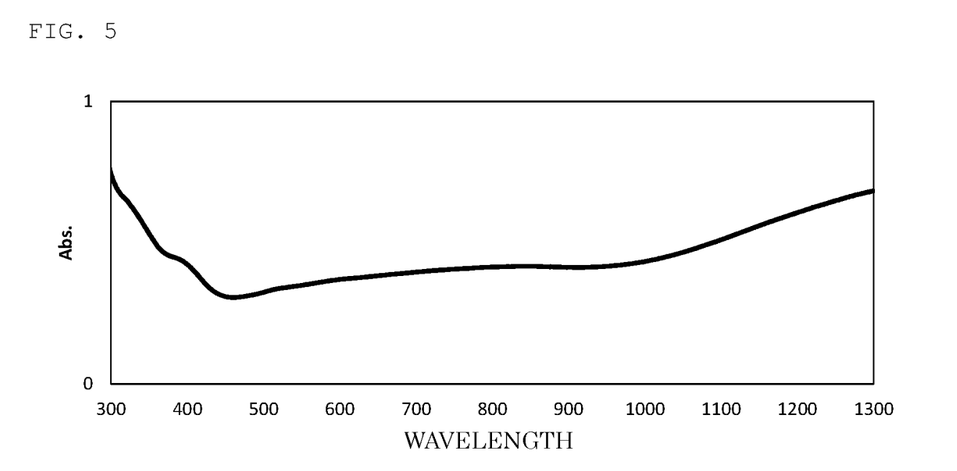
FIG. 5 is an ultraviolet-visible-near infrared absorption spectrum of an aqueous solution obtained in Example 8.

The product is water soluble, and can be prepared into an aqueous solution through film formation and subsequent washing with water. An ultraviolet-visible-near infrared absorption spectrum of the resultant polymer is shown in FIG. 5. The solution was dark blue, and in the ultraviolet-visible-near infrared absorption spectrum, peaks shifted to longer wavelengths (nm). It is considered that the compound having —$SO_3^-Na^+$ in the molecule produced in Example 2 was polymerized despite the absence of an oxidant.

INDUSTRIAL APPLICABILITY

The homopolymer represented by the formula (3) produced by the method of the present invention is a conductive polymer that is water soluble and excellent in processability. Accordingly, the homopolymer is useful as any of various conductive materials or optical materials, such as an electrode, a sensor, an electronic display device, a nonlinear optical device, an optical conversion device, and an antistatic agent, which require precision processing.

The invention claimed is:

1. A fused heteropolycyclic compound, which is represented by the following formula (1):

(1)

where: $R^1$, $R^2$, $R^3$, $R^4$, and $R^5$ each independently represent a monovalent substituent selected from the group consisting of (1) a hydrogen atom, (2) a linear or branched alkyl group having 1 to 20 carbon atoms, a linear or branched alkoxy group having 1 to 20 carbon atoms, or a linear or branched alkyl ester group (alkylcarbonyloxy group or alkoxycarbonyl group) having 1 to 20 carbon atoms, (3) $SO_2M$, (4) a halogen atom, (5) a carboxy group, (6) a phosphonyl group, (7) a nitro group, (8) a cyano group, (9) a primary, secondary, or tertiary amino group, (10) a trihalomethyl group, (11) a phenyl group, and (12) a phenyl group substituted with at least one selected from an alkyl group, a hydroxy group, an alkoxy group, an alkyl ester group, a carbonyl group, a sulfo group, and a halogen atom; hydrocarbon chains in the substituents represented by $R^1$, $R^2$, $R^3$, $R^4$, and $R^5$ may be bonded to each other at any positions to form at least one divalent chain forming at least one cyclic structure of a three- to seven-membered cyclic saturated or unsaturated hydrocarbon together with carbon atoms to which the substituents are bonded; the alkyl group, the alkoxy group, or the alkyl ester group represented by each of $R^1$, $R^2$, $R^3$, $R^4$, and $R^5$, or the cyclic hydrocarbon chain formed thereby may contain at least one bond selected from a carbonyl, an ether, an ester, an amide, a sulfide, a sulfinyl, a sulfonyl, and an imino; M represents OH, or an alkali metal alkoxide selected from $O^-Na^+$, $O^-Li^+$, and $O^-K^+$, an ammonium alkoxide represented by $O^-NH_4^+$, a linear or branched alkoxy group having 1 to 20 carbon atoms, or a halogen atom selected from chlorine, fluorine, bromine, and iodine; and k represents the number of fused rings sandwiched between a heterocycle and a benzene ring having the substituents $R^1$ to $R^3$, and represents an integer of from 0 to 3.

2. The fused heteropolycyclic compound according to claim 1, wherein k in the formula (1) represents 0.

3. The fused heteropolycyclic compound according to claim 1, wherein M in the formula (1) is selected from OH, $O^-Na^+$, $O^-Li^+$, $O^-K^+$, and $O^-NH_4^+$.

4. The fused heteropolycyclic compound according to claim 1, wherein $R^1$, $R^2$, $R^3$, $R^4$, and $R^5$ in the formula (1) each independently represent a monovalent substituent selected from (1) a hydrogen atom, (2) a linear or branched alkyl group having 1 to 20 carbon atoms, a linear or branched alkoxy group having 1 to 20 carbon atoms, or a linear or branched alkyl ester group having 1 to 20 carbon atoms, (3) $SO_2M$, and (4) a halogen atom.

5. A method for producing the fused heteropolycyclic compound of claim 1, the method including allowing an oxidant to act on a compound represented by the following formula (1A):

(1A)

where: $R^1$, $R^2$, $R^3$, $R^4$, $R^5$, and M represent the same meanings as described for the formula (1); and k represents a number of fused rings sandwiched between a heterocycle and a benzene ring having the substituents $R^1$ to $R^3$, and represents an integer of from 0 to 3.

* * * * *